United States Patent [19]

Bouffard et al.

[11] Patent Number: 5,914,313
[45] Date of Patent: *Jun. 22, 1999

[54] 1-[4-HYDROXY-5-AMINOETHYLOXY-$N^2$-(10, 12-DIMETHYL-1-OXOTETRADECYL) ORNITHINE]-5-(3-HYDROXYGLUTAMINE)-6-(3-HYDROXYPROLINE)ECHINOCANDIN B, OTHER AMINOALKYL DERIVATIVES AND SALTS THEREOF

[75] Inventors: Frances Aileen Bouffard, Scotch Plains; James F. Dropinski, Piscataway, both of N.J.

[73] Assignee: Merck & Co., Inc., Rahway, N.J.

[ * ] Notice: This patent is subject to a terminal disclaimer.

[21] Appl. No.: 08/005,942

[22] Filed: Jan. 15, 1993

Related U.S. Application Data

[63] Continuation-in-part of application No. 07/775,773, Oct. 17, 1991, abandoned, and application No. 07/960,983, Oct. 16, 1992.

[51] Int. Cl.$^6$ .............................. A61K 38/12; C07K 7/50
[52] U.S. Cl. .................... 514/11; 514/9; 514/2; 530/317; 530/318
[58] Field of Search ...................... 514/11, 9, 2; 530/317, 530/318

[56] References Cited

U.S. PATENT DOCUMENTS

| | | | |
|---|---|---|---|
| 4,117,118 | 9/1978 | Harri et al. | 530/317 |
| 4,293,491 | 10/1981 | Debono | 530/317 |
| 4,304,716 | 12/1981 | Abbott et al. | 530/317 |
| 4,931,352 | 6/1990 | Fromtling et al. | |
| 4,968,608 | 11/1990 | Giacobbe et al. | |
| 5,166,135 | 11/1992 | Schmatz | 530/317 |
| 5,202,309 | 4/1993 | Schwartz et al. | 514/11 |

FOREIGN PATENT DOCUMENTS

| | | |
|---|---|---|
| 851 310 | 8/1977 | Belgium . |
| 859 067 | 3/1978 | Belgium . |
| 0 447 186 | 3/1991 | European Pat. Off. . |
| 0 451 957 | 3/1991 | European Pat. Off. . |
| 0 459 564 | 5/1991 | European Pat. Off. . |
| 3-163096 | of 0000 | Japan . |
| 2065130 | 6/1981 | United Kingdom . |

OTHER PUBLICATIONS

Keller–Juslen, et al, Chem. Abtract, 89, AB 129931w (1978).
Keller–Juslen, et al, Chem. Abstract, 88, AB 7377d (1978).
A.A. Adefarati, et al, Chem. Abstract, 114, No. 21, p. 441, AB #203–279t.

*Primary Examiner*—Ponnathapura Achutamurthy
*Assistant Examiner*—J. D. Wessendorf
*Attorney, Agent, or Firm*—Elliott Korsen; Mark R. Daniel

[57] ABSTRACT

A compound having the formula

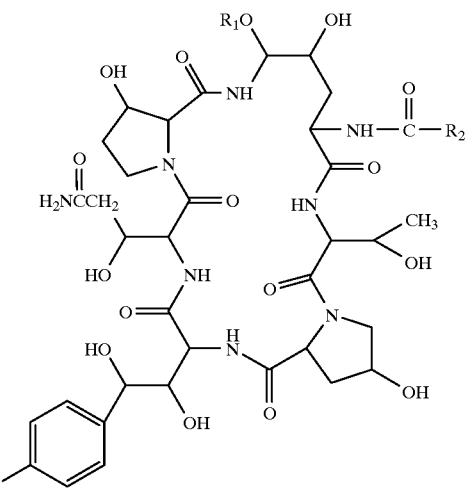

in which $R_1$ is an aminoalkyl group and

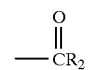

is an acyl group and salts thereof having high antibiotic activity and being substantially free of lytic activity are described.

15 Claims, No Drawings

1-[4-HYDROXY-5-AMINOETHYLOXY-$N^2$-(10, 12-DIMETHYL-1-OXOTETRADECYL) ORNITHINE]-5-(3-HYDROXYGLUTAMINE)-6-(3-HYDROXYPROLINE)ECHINOCANDIN B, OTHER AMINOALKYL DERIVATIVES AND SALTS THEREOF

This is a continuation-in-part of application Ser. No. 07/775,773, filed Oct. 17, 1991 abandoned, and Ser. No. 07/960,983, filed Oct. 16, 1992 copending.

BACKGROUND OF THE INVENTION

The present invention is directed to antibiotic compounds having a superior combination of properties.

Echinocandin B and related fermentation metabolites are known to have antifungal properties when tested in vitro. However, some of the compounds are toxic when tested in vivo and some show lytic activity on human red blood cells thus rendering them undesirable for therapeutic use. Some derivatives have been prepared in a search to find more useful compounds for human therapeutic use. Most of the derivatives are lipophilic side chain analogs at the α-amino-nitrogen of the hydroxyornithine residue or ethers at the hemiaminal position. A number of aminoalkyl ethers were prepared and are the subject of Belgian patent No. 859,067 (1978) and Belgian patent No. 851,310 (1977).

According to the present invention it has been discovered that when the aminoalkyl ether is that derived not from echinocandin B but from a cyclohexapeptide compound in which one of the nuclear amino acids is glutamine instead of threonine, the compound has superior antibiotic activity in vivo. Moreover, the compound is substantially non-toxic and also non-lytic toward human blood cells, thereby rendering the compound adaptable for human therapy which has not been possible with many compounds even though they might be active.

The compounds of the present invention are aminoalkyl ethers at the 5-position of ornithine and acyl derivatives at the $N^2$ position of the ornithine in the cyclopeptide nucleus and which may be represented by the formula (I) (SEQ ID NO 1)

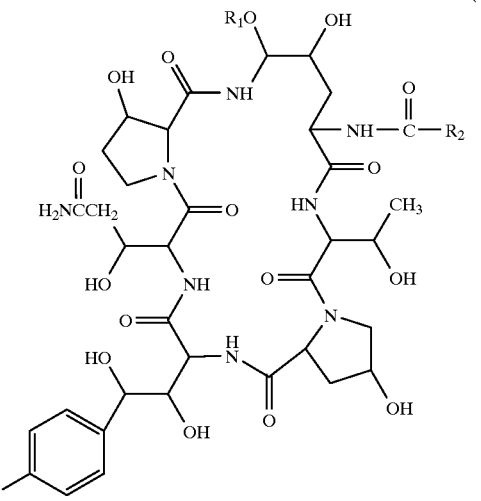
(I)

In this and succeeding formulas, $R_1$ is  —$CH_2CH(NH_2)CH_2R^I$
 —$C_nH_{2n}NR^{II}R^{III}$
 —$(CH_2)_{1-3}CH(NH_2)R^{IV}$ or
 —$C_nH_{2n}NHR^V$ wherein n is 2 to 6;

$R_2$ is  - $C_9$–$C_{21}$ alkyl,
 - $C_9$–$C_{21}$ alkenyl,
 - $C_1$–$C_{10}$ alkoxyphenyl, or
 - $C_1$–$C_{21}$ alkoxynaphthyl;

$R^I$ is  —OH
 —$NH_2$
 —NHC(=NH)$NH_2$
 —NHC(=NH)$(CH_2)_{0-3}$H $R^{II}$ is  —H
 - $C_1$–$C_4$ alkyl or
 - benzyl $R^{III}$ is  —H
 - $C_1$–$C_4$ alkyl
 - benzyl or
 $R^{II}$ and $R^{III}$ together are —$(CH_2)_4$— or —$(CH_2)_5$—

$R^{IV}$ is  - $C_1$–$C_4$ alkyl
 —$CONH_2$

-continued $R^V$ is
—C(=NH)NH$_2$
—C(=NH)(CH$_2$)$_{0-3}$H
—(CH$_2$)$_{2-4}$NH$_2$
—(CH$_2$)$_{2-4}$OH
—CO(CH$_2$)$_{1-3}$NH$_2$
—(CH$_2$)$_{2-4}$NH(C=NH)NH$_2$
—(CH$_2$)$_{2-4}$NH(C=NH)(CH$_2$)$_{0-3}$H

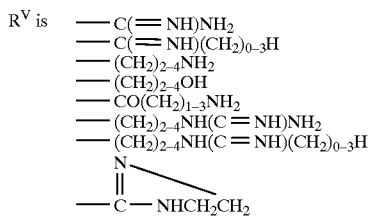

Salts of the foregoing are also within the scope of the present invention. Salts include acid addition salts and quaternary ammonium salts. These salts are formed at the amino function of the amino alkyl group.

Pharmaceutically acceptable salts as acid addition salts are those from acids such as hydrochloric, hydrobromitc, phosphoric, sulfuric, maleic, citric, acetic, tartaric, succinic, oxalic, malic, glutamic, salicylic, lactic, gluconic, hydrocarbonic and the like, and include other acids related to the pharmaceutically acceptable salts listed in Journal of Pharmaceutical Science, 66, 2 (1977).

The compounds in the scope of the present invention which have a highly desirable combination of properties of high effectiveness and/or low toxicity and other adverse side reactions are all aminoalkyl ethers at the 5-hydroxy position of the 4,5-dihydroxyornithine component of the cyclopeptide. The amino group may be substituted or the alkyl portion may have other substituents but it is critical that the basic amino property of the group be retained.

The acyl substituent on the ornithine nitrogen may be varied from that of the natural product. Thus, the side chain radical which together with carbonyl forms the acyl group may be alkoxy substituted phenyl or naphthyl as well as being derived from a long chain fatty acid.

Certain compounds may be named as echinocandins or pneumocandins. The pneumocandins, compounds in which one of the amino acids of the cyclic peptide is glutamine instead of a second threonine and the side chain on the ornithine nitrogen is 10,12-dimethylmyristoyl have been named as pneumocandins by Schwartz et al, J. Antibiot. 45, No. 12, 1853–1866 (1992), and also found in J. M. Balkovec et al, Tetrahedron Let., 1992, 33, 4529–32. Thus, the natural product in which the nucleus is 4,5-dihydroxyornithine, threonine, 4-hydroxyproline, 3,4-dihydroxyhomotyrosine, 3-hydroxy glutamine and 3-hydroxyproline and the side chain is 10,12-dimethylmyristoyl is named pneumocandin B$_0$. Compounds of the present invention which differ only in the substituent at the 5-hydroxy of ornithine may be named as derivatives of pneumocandin B$_0$ although for the compound of the parent application which was named as an echinocandin, the echinocandin name is given.

The compounds of the present invention are white solids soluble in a variety of organic solvents such as methanol, ethanol, dimethylformamide (DMF), dimethylsulfoxide (DMSO) and the like and also in water.

The antibiotic activity disclosed above is especially of note against fungi causing pathogenic mycotic infections such as *Candida albicans, Candida tropicalis*, and the like, *Aspergillus fumigatus* and other Aspergillus sp. Compound I has been found to significantly prolong the survival of mice infected with *Candida albicans* and also to eradicate *Candida albicans* from kidneys of experimentally infected mice. These properties point to a new antifungal drug with great potential in the therapy of human mycotic infections. Additionally, the compound is adapted to be employed for inhibiting or alleviating *Pneumocystis carinii* infections, prevalent in immune compromised patients and which have usually been fatal.

The structural aspect which distinguish the compounds of the present invention and which confer the foregoing desirable properties is the combination of the aminoalkyl group on the 5-hydroxyornithine of the cyclopeptide nucleus and the carboxamide group arising from the nuclear amino acid glutamine. For the desirable combination of properties, the amino acids of the nucleus are not changed. The aminoalkyl group may be varied provided that the aminoalkyl always has a basic amino group and certain acyl groups may replace the 10,12-dimethylmyristoyl group on the α-nitrogen of the ornithine, but these modifications are those which do not affect the fundamental and essential amino acids of the cyclopeptide.

The compounds of the present invention may be prepared by aminoalkylation of a natural product cyclopeptide or a derivative of a natural product which is represented by the formula (A) (SEQ ID NO. 1)

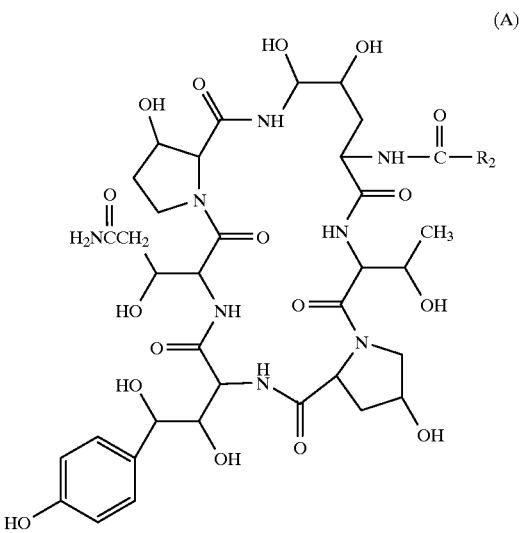

(A)

with an aminoalkanol (or alkanolamine), R$_1$OH wherein R$_1$ is an aminoalkyl group in which the amino may be substituted or unsubstituted. When it is a substituted amino group, the substituent is such that it does not neutralize the basic amino group. The aminoalkylation is carried out in the presence of a strong acid in an aprotic polar solvent and the product isolated from the reaction mixture preferably by the use of reverse phase high performance liquid chromatography (HPLC).

The nucleus of the aminoalkyl ether and the starting material are the same since the amino acids of the peptide nucleus are not changed. Thus, both product and starting material have the same Sequence ID number.

R$_1$OH may be substituted or unsubstituted. When unsubstituted, a protecting group optionally is placed on the amino group before the reaction is carried out and the protecting group removed after the etherification is complete as hereinafter more fully described. When R$_1$ is a substituted amino group, a substituted amino alcohol may be the reactant or alternatively an unsubstituted amino alcohol may be employed and the substituent subsequently put on the amino group.

The amino alcohol is generally employed in the form of an acid addition salt and is employed in an amount of from about 20 to 200 equivalents.

The reaction is carried out in the presence of a strong acid. Examples of strong organic acids are camphorsulfonic acid, p-toluenesulfonic acid, methanesulforiic acid or a mineral acid such as hydrochloric or hydrobromic acid. Hydrochloric and camphorsulfonic acids are preferred. Approximately 1 equivalent of the acid is employed.

A solvent is employed in carrying out the reaction. Suitable solvents are aprotic solvents and include dimethylsulfoxide (DMSO), dimethylformamide (DMF), 1-methyl-2-pyrrolidinone, hexamethylphosphoric triamide (HMPA), dioxane or combinations thereof. Dimethyl sulfoxide and dimethylformamide is preferred.

When the amino alcohol has a primary amino group, the group may be protected before it is used. Conventional protecting groups are employed. The carbobenzyloxy group (CBz) is the preferred group. In protecting the amino group with a carbobenzyloxy group, the group is placed on the amino group of $R_1OH$ by conventional means and the protected $R_1OH$, the cyclopeptide to be etherified and a strong acid, as used in the etherification using an unprotected $R_1OH$, are stirred together in a solvent such as those useful in the reaction employing an unprotected amino alcohol until substantial completion of the reaction. The progress of the reaction may be monitored by HPLC. After completion of the reaction, the reaction mixture is neutralized, diluted with water and then purified by HPLC to obtain an N-benzyloxycarbonyl aminoalkyl ether intermediate.

To obtain the desired aminoalkyl ether, the protected ether is hydrogenated under balloon pressure in the presence of palladium/carbon in acetic acid, preferably for from one to several hours as may be monitored by analytical HPLC with 30 to 40 percent aqueous acetonitrile solvent system containing 0.1% trifluoroacetic acid. The product is then recovered by first removing the catalyst and lyophilizing the filtrate to obtain the desired product as acetate salt. The latter may be converted to a hydrochloride by passing a minimum volume aqueous solution thereof through an anion exchange column.

With substituted amino groups, if the substituent is not already on the amino alcohol, it may be placed on the amino group after the ether is formed by a method appropriate for the particular group and within the knowledge of the skilled in the art.

The ether product is isolated from the reaction mixture and is conveniently purified using HPLC techniques, including utilization of a reverse phase column. The eluants from HPLC are then concentrated and lyophilized as subsequently detailed. The elution is carried out using various concentrations of acetonitrile/water, starting at about 15 percent acetonitrile and then increasing the amount of acetonitrile. The eluting solutions generally contain 0.1 percent trifluoroacetic acid (TFA) or acetic acid and the product on isolation is found in the form of the salt.

When quaternary ammonium salts are desired, the amino alkyl product is reacted with excess alkyl halide by stirring in a conventional manner until substantial amounts of the product is obtained, the reaction mixture diluted with water and chromatographed according to conventional procedures.

The compounds of the present invention are active against many fungi and as previously indicated particularly against Candida species. The antifungal properties may be illustrated with the minimum fungicidal concentration (MFC) determination against certain Candida organisms in a microbroth dilution assay carried out in a Yeast Nitrogen Base (Difco) medium with 1 percent dextrose (YNBD).

In carrying out the assay, Compound I was solubilized in 10 percent dimethyl sulfoxide (DMSO) and diluted to 2560 μg/ml. The compound was then diluted to 256 μg/ml in YNBD. 0.15 mL of the suspension was dispensed to the top row of a 96-well plate (each well containing 0.15 ml of YNBD) resulting in a drug concentration of 128 μg/ml. Two-fold dilutions were then made from the top row to obtain final drug concentrations ranging from 128 to 0.06 μg/ml.

The yeast cultures, maintained on Sabouraud dextrose agar were transferred to YN broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 ml per well yielding a final inoculum per well of $1.5-7.5 \times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 μl samples from the wells in the 96-well microplate were transferred to a single well tray containing Sabouraud dextrose agar. The inoculated trays were incubated 24 hours at 28° C. and then read for minimum fungicidal concentration (MFC). MFC is defined as the lowest concentration of drug showing no growth or less than 4 colonies per spot. The results showed the minimum fungicidal concentration against *Candida albicans* MY 1055 and against *Candida tropicalis* MY 1012 to be as follows:

| | | MFC μg/mL | |
|---|---|---|---|
| $R_1$ | $R_2$ | C. albicans MY 1055 | C. tropicalis MY 1012 |
| —CH$_2$CH$_2$—NH—C(=NH)NH$_2$ | DMTD* | 0.125 | 0.125 |
| —CH$_2$CH$_2$N$^+$(CH$_3$)$_3$ I$^-$ | DMTD | 0.25 | 0.25 |
| —CH$_2$CH$_2$NHCOCH$_2$NH$_2$ | DMTD | 1.0 | 0.5 |
| —CH$_2$CH$_2$NH$_2$ | DMTD | 0.125 | 0.25 |
| —CH$_2$CH$_2$NH$_2$ | C$_6$H$_4$OC$_8$H$_{17}$(p) | 0.5 | 0.5 |

*DMTD = 9,11-dimethyltridecyl

In a separate similar experiment with different compounds against *Candida albicans* MY 1750, the following results were obtained:

| $R_1$ | $R_2$ | MFC $\mu$g/mL C. albicans MY 1750 |
|---|---|---|
| —CH$_2$CH(NH$_2$)CH$_3$ | DMTD | 0.50 |
| —CH$_2$CH$_2$NHC$_2$H$_5$ | DMTD | 0.50 |
| —CH$_2$CH(OH)CH$_2$NH$_2$ | DMTD | 0.50 |
| —CH$_2$CH$_2$NH—C(=NH)CH$_3$ | DMTD | 0.25 |
| —CH$_2$CH$_2$NHCOCH$_2$NH$_2$ | DMTD | 0.50 |
| —CH$_2$CH(NH$_2$)CH$_2$NH$_2$ | DMTD | 2.0 |

The compounds also show in vivo effectiveness against fungi as seen by the following experiment carried out on the compound on which $R_1$ is —CH$_2$CH$_2$NH$_2$.

Growth from an overnight SDA culture of *Candida albicans* MY 1055 was suspended in sterile saline and the cell concentration determined by hemacytometer count and the cell suspension adjusted to 3.75×10$^5$ cells/ml. Then 0.2 milliliter of this suspension was administered I.V. in the tail vein of mice so that the final inoculum was 7.5×10$^4$ cells/mouse.

The assay then was carried out by administering aqueous solutions of Compound I ($R_1$ =—CH$_2$CH$_2$NH$_2$) at various concentrations intraperitoneally (I.P.), twice daily (b.i.d.) for four consecutive days to 18 to 20 gram female DBA/2 mice, which previously had been infected with *Candida albicans* (MY 1055) in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per-gram of kidneys. Compound I showed greater than 99 percent reduction of recoverable Candida CFUs at 0.4 mg/kg I.P. twice daily for four consecutive days.

A harmful and potentially fatal side reaction of a number of drugs including certain antibiotically active echinocandin compounds is red blood cell lysis. It is of particular interest that representative compounds of this invention exhibit no red blood cell lysis at concentrations far beyond what would be used for therapeutic purposes. The blood cell lysis property may be seen in the determination carried out in the following manner.

The blood employed is a 4 percent suspension of freshly drawn heparinized blood prepared by adding 2 milliliters of blood to 50 milliliters of sterile 5 percent dextrose.

Compoufid I was solubilized in a small volume of dimethylsulfoxide (DMSO) that was then diluted with distilled water to a final concentration of 5 percent DMSO to obtain a drug solution of 4.0 mg/ml. A 0.2 milliliter amount of the drug solution was added to 1.4 milliliters of sterile 5 percent dextrose to obtain the test solution. A diluent control was also prepared.

A 96-well microtiter plate with a well volume of 0.35 ml was used for the assay. Columns 2–12 were filled with 150 $\mu$l of sterile 5 percent dextrose. Then, 300 $\mu$l of test solutions were dispensed into the wells in column 1 and serially two-fold diluted in 5 percent dextrose to yield final test concentrations of from 400 to 0.20 $\mu$g/ml. 38 $\mu$l of red blood cell suspension were added to each well, the plate was gently agitated to mix the well contents and incubated at room temperature for 2 hours, and thereafter observed to determine extent of hemolysis as indicated by complete or partial clearing (lysis).

Minimum lytic concentration (MLC) defined as the lowest concentration of test compound to produce complete or partial lysis of red blood cells was found for representative compounds against human blood cells to be as seen in the following table:

| $R_1$ | $R_2$ | MLC ($\mu$g/ml) |
|---|---|---|
| —CH$_2$CH(NH$_2$)CH$_3$ | DMTD | 400 |
| —CH$_2$CH$_2$NHC$_2$H$_5$ | DMTD | >400 |
| —CH$_2$CH(OH)CH$_2$NH$_2$ | DMTD | >400 |
| —CH$_2$CH$_2$NHC(=NH)CH$_3$ | DMTD | 200 |
| —CH$_2$CH$_2$NHCOCH$_2$NH$_2$ | DMTD | >400 |

The compounds of the present invention may also be useful for inhibiting or alleviating *Pneumocystis carinii* infections in immune compromised patients. The efficacy of the compounds of the present invention for the therapeutic or anti-infective purposes may be demonstrated in studies on immunosuppressed rats in which Sprague-Dawley rats (weighing approximately 250 grams) are immunosuppressed with dexasone in the drinking water (2.0 mg/L) and maintained on a low protein diet for seven weeks to induce the development of pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound I in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic examination of stained slides for the presence of cysts. The prevention of or reduction of cysts are seen in slides of lungs of treated rats when compared with the number of cysts in lungs of untreated controls or solvent controls.

The dosage required for 90 percent reduction of cysts with representative compounds may be seen in the following table:

| $R_1$ | $R_2$ | mg/kg |
|---|---|---|
| —CH$_2$CH(NH$_2$)CH$_3$ | DMTD | <0.08 |
| —CH$_2$CH$_2$NHC$_2$H$_5$ | DMTD | 0.04 |
| —CH$_2$CH$_2$NHC(=NH)CH$_3$ | DMTD | <0.08 |
| —CH$_2$CH$_2$NHCOCH$_2$NH$_2$ | DMTD | 0.04 |

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound I or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired. Compositions formulated for oral administration may be a liquid composition or a solid composition. For liquid preparations, the therapeutic may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, koalin, talc, lactose, generally with lubricant, such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. The compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 10 to 200 milligrams of one of the compounds.

When the compound is for antifungal use any method of administration may be employed. For treating mycotic infections, oral administration is frequently preferred.

When the compound is to be employed for control of pneumocystis infections, it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol which may be formulated as a suspension of Compound I in a suitable propellant such as fluorocarbon or hydrocarbons.

The following examples illustrate the preparation of Compound I and compositions of Compound I useful in the therapeutic application of Compound I, but are not to be construed as limiting.

EXAMPLE 1

1-[4-hydroxy-5-aminoethyloxy-$N^2$-(10,12-dimethyl-1-oxotetradecyl)ornithine]-5-(3-hydroxyglutamine)-6-(3-hydroxyproline) echinocandin B trifluoroacetate

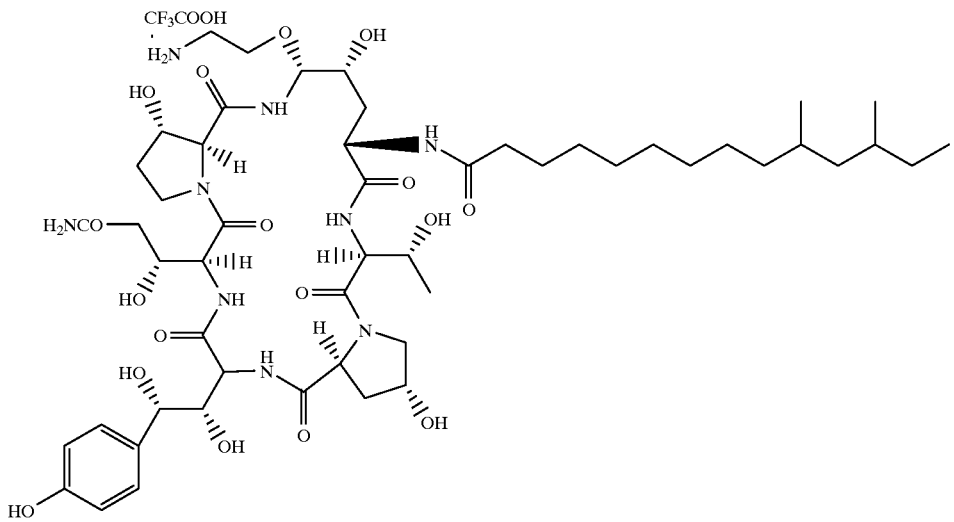

Seq ID No 1

A solution of 200 milligrams (0.19 mmol) of 1-[4,5-dihydroxy-$N^2$-(10,12-dimethyl-1-oxotetradecyl)-ornithine]-5-(3-hydroxyglutamine)-6-(3-hydroxyproline) echinocandin B or pneumocandin $B_o$ (Seq. I.D. No. 1), 1.83 grams of ethanolamine hydrochloride (19 mmol), and 44 milligrams (0.19 mmol) of (1S)-(+)-10-camphorsulfonic acid in 8 milliliters of anhydrous dimethylsulfoxide was stirred at 25° C.

for a period of 4 days. The reaction mixture was diluted with 16 milliliters of water and flash chromatographed on a "LICHROPREP"(E. Merck) RP-18(40–63 μm,8 g) column, packed in 15 percent acetonitrile/water. The column was then eluted first with 15 percent acetonitrile/water (2×100 mL) then with 35 percent acetonitrile/water. The fractions from the latter elution were combined, concentrated and lyophilized to obtain 65 milligrams of product. The latter was purified by preparative HPLC ["ZORBAX" (DuPont) C18, 21.2×250 mm, 40 percent acetonitrile/water (0.1% $CF_3COOH$)], and the eluates concentrated and lyophilized to obtain the product of the above formula (SEQ ID NO 1). The product has the following spectral characteristics:

$^1$H NMR Spectra (400 MHz, $CD_3OD$) δ 1.16 (d, 3, J=6.2 Hz, $CH_3$-threo), 3.12 (m, 2, $OCH_2CH_2NH_2.CF_3COOH$), 3.72 (m, $OCH_2CH_2NH_2.CF_3COOH$), 4.10 (m, 1, H4 4,5-(di-OH)-orn), 5.24 (d, 1, J=2.3 Hz, H5 4,5-(di-OH)-orn); FAB-MS, m/e 1108 $(M+1)^+$

EXAMPLE 2

Seq ID No 1

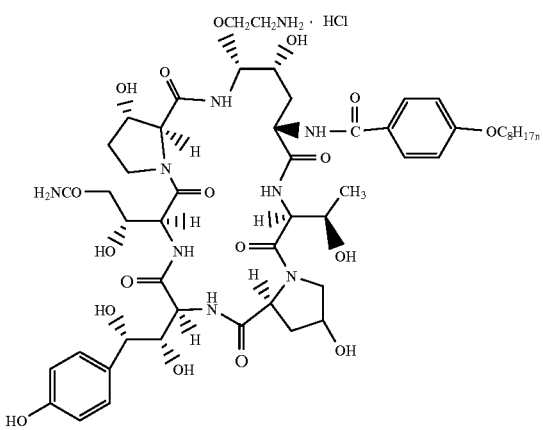

Part A

N-Benzyloxycarbonylaminoethyl Ether (SEQ ID NO 1)

A solution of 3.5 grams (3.31 mmol) of 1-[4,5-dihydroxy-$N^2$-(4-octyloxybenzoyl)ornithine]-5-(3-hydroxyglutamine)-6-(3-hydroxyproline) echinocandin B, 16.13 grams (82.7 mmol) 2-(N-benzyloxycarbonylamino)ethanol and 768 milligrams (3.31 mmol) of (1S)-(+)-10-camphorsulfonic acid in 120 mL of anhydrous dixane and 12 mL of anhydrous N,N-dimethylformamide was stirred at 25° C. The reaction was monitored by analytical HPLC using "ZORBAX" RX-C18 column and a solvent system of 55% $CH_3CN/H_2O$ at a flow rate of 1.5 mL/min with UV detection at 210 and 277 nm. After about 20 hours >95 percent conversion to product ($t_R$=3.76 min) was noted. The reaction mixture was neutralized by the addition of 3.5 mL of 1M $NaHCO_3$ and then diluted with 135 mL of $H_2O$. The resulting solution was filtered and the filtrate pump-injected onto a "DELTA-PAK" C18 cartridge column (47 mm×30 cm) and eluted using step gradient (45–55% $CH_3CN/H_2O$) elution at a flow rate of 50 mL/min. The appropriate fractions were combined, diluted with 250 milliliters of water and the product recovered by solid-phase extraction using the same column in 5% $CH_3CN/H_2O$. The extracted material was pump-injected onto the column, then eluted with 95% $CH_3CN/H_2O$, the product containing eluates pooled, concentrated and lyophilized to obtain the N-benzyloxycarbonylaminoethyl ether intermediate in a yield of 2.3 grams (56%) as a white amorphous solid: HPLC assay at 210 nm >97% product. Mass spectrum: (FAB) 1242.7 $(M+Li)^+$ Part B Aminoethyl Ether($R_1$=HCl.$NH_2CH_2CH_2$—)

A solution of 2.30 grams (1.86 mmol) of the N-benzyloxycarbonylaminoethyl ether prepared in Part A in 25 milliliters of acetic acid was hydrogenated under balloon pressure in the presence of 1.80 g 10% Pd/C for a period of 1.5 hours. The reaction was monitored by analytical HPLC and a solvent system of 35% $CH_3CN/H_2O$ at a flow rate of 1.5 mL/min with UV detection 210 and 277 nm. Complete conversion to a product peak at $t_R$=5.46 min. was observed. The reaction mixture was filtered to remove the catalyst and the filtrate was lyophilized to obtain the aminoethyl ether as the acetate salt. The lyophilizate was dissolved in a minimum volume of $H_2O$ and the solution was passed through a column of anion exchange resin (Bio-Rad AG2-X8(Cl-)) and the eluate was lyophilized to obtain 2.0 grams (95% yield) of the compound of above formula as a white amorphous solid.

Mass spectrum (FAB) 1109.0 $(M+Li)^+$

EXAMPLE 3

Seq ID No 1

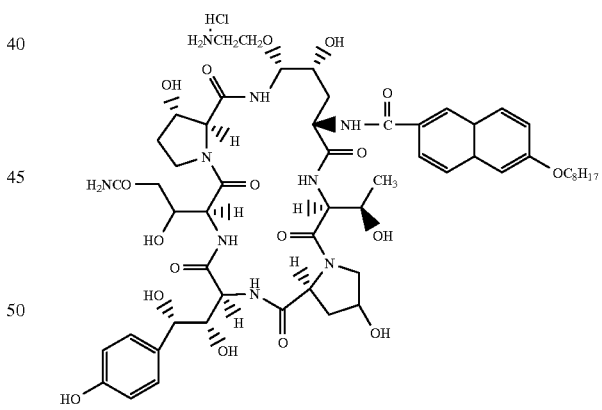

Preparation of Starting Cyclopeptide Derivative

Pentafluorophenyl 6-octyloxy-2-naphthoate for acylating the cyclopeptide was first prepared in the following manner: To a suspension of 6-octyloxy-2-naphthoic acid (3.15 g, 10.5 mmol) and dicyclohexylcarbodiimide in ethyl acetate (25 mL) at 0° C. was added pentafluorophenol (2.12 g, 11.5 mmol). The mixture was stirred at 25° C. for a period of 18 hours. The precipitate was removed by filtration. The filtrate was washed with water (2×150 mL) and brine and dried with magnesium sulfate. Removal of the ethyl acetate in vacuo yielded 5.4 g of pentafluorophenyl 6-octyloxy-2-naphthoate as a yellow solid: $^1$H NMR (400 MHz, CD$_3$OD) δ 0.88 (t, 3, J=6.9 Hz), 4.10 (t, 2, J=6.6 Hz), 7.16 (d, 1), 7.21 (d, 1), 7.80 (d, 1), 7.87 (d, 1), 8.08 (dd, 1), 8.69 (d, 1).

2.0 grams (4.29 mmol) of pentafluorophenyl 6-octyloxy-2-naphthoate, thus prepared, was added to 2.0 grams of 33 percent by weight (0.799 mmol) of 1-(4,5-dihydroxy-ornithine)-5-(3-hydroxyglutamine)6-(3-hydroxyproline) echinocandin B in 50 milliliters of anhydrous DMF. HPLC analysis, eluting with 45% CH$_3$CN/H$_2$O at 1.5 mL/min and detection at 210 and 277 nm showed conversion to product peak at $t_R$=5.90 min after 18 hours. The DMF was removed in vacuo and the residue triturated with two 100 milliliter portions of diethyl ether. Reverse-phase flash chromatography of the triturate eluting with 40–45% CH$_3$CN/H$_2$O and then lyophilizing the appropriate fractions produced 340 milligrams of 1-[4,5-dihydroxy-N$^2$-(6-octyloxy-2-naphthoyl)ornithine]-5-(3-hydroxyglutamine)-6-(3-hydroxyproline)echinocandin B (80% purity). A 40 mg portion was rechromatographed on "ZORBAX" with 43 percent CH$_3$CN/H$_2$O at 10 ml/min, uv detection at 220 nm to obtain 30 mg of N-acylated compound of >98 percent purity.

Mass spectrum: FAB 1116.0 (M+Li)$^+$

Part A

N-Benzyloxycarbonylaminoethyl Ether

To a solution of 300 mg (80% purity, 0.271 mmol) of the 6-octyloxy-2-naphthoyl starting material above prepared, 1.4 grams (7.18 mmol) of 2-(N-benzyloxycarbonylamino) ethanol and 62.9 mg (0.271 mmol) of (1S)-(+)-10-camphorsulfonic acid in 10 ml anhydrous dioxane and 1 mL anhydrous DMF was stirred at 25° C. HPLC analysis using 65% CH$_3$CN/H$_2$O at 1.5 mL/min with detection at 210 and 277 nm indicated. after 18 hours a greater than 95 percent conversion to a less polar product ($t_R$=3.36 min). The reaction was quenched with 1M NaHC0$_3$, the reaction mixture diluted with water and subjected to reverse-phase flash chromatography eluting with 40–60 percent CH$_3$CN/H$_2$O in 10% step gradients to obtain after lyophilization of the 60 percent fractions, ether

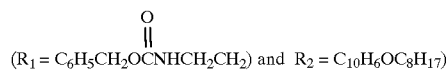
(R$_1$ = C$_6$H$_5$CH$_2$OCNHCH$_2$CH$_2$) and R$_2$ = C$_{10}$H$_6$OC$_8$H$_{17}$)

Part B

Aminoethyl Ether

In a manner similar to that described in Example 2, a solution of 180 mg (70% purity, 0.140 mmol) in 10 ml of acetic acid was hydrogenated under balloon pressure in the presence of 160 mg 10% Pd/C for a period of 1.5 hours. The reaction was monitored by analytical HPLC using 40% CH$_3$CN/H$_2$O at a flow rate 1.5 mL/min with detection at 210 and 277 nm. Conversion (>95%) to a more polar product peak ($t_R$=6.43 min) was observed after 1 hour. The reaction mixture was filtered to remove catalyst and the filtrate concentrated in vacuo. Preparative HPLC of the filtrate using "DELTAPAK" at 10 mL/min, followed by lyophilization of the appropriately combined eluates produced 30 mg of 99% pure and 80 mg of 90% pure aminoethyl ether as the trifluoroacetate salt as a white amorphous solid. The 90 percent pure material was rechromatographed on "ZORBAX" and eluted with 30–35% CH$_3$CN/H$_2$O with detection at 220 nm to obtain another 35 mg of product of >98% purity. Total yield 58%.

Mass spectrum: (FAB) 1158.5 (M+Li)$^+$

EXAMPLE 4

1-[4-Hydroxy-5-aminoethyloxy-N$^2$-(10,12-dimethyl-1-oxotetradecyl)ornithine]-5-(3-hydroxyglutamine)-6-(3-hydroxyproline)echinocandin B trifluoroacetate (SEQ ID NO 1)

Part A

N-Benzyloxycarbonylaminoethyl Ether

In a manner similar to that described in Example 2, a solution of 1-[4,5-dihydroxy-N$^2$-(10,12-dimethyl-1-oxotetradecyl)ornithine]-5-(3-hydroxyglutamine)-6-(3-hydroxyproline)echinocandin B trifluoroacetate, 2-(N-benzyloxycarbonylamino)ethanol and (1S)-(+)-10-camphorsulfonic acid were stirred at ambient temperature to obtain 1-[4-hydroxy-5-(2-N-benzyloxycarbonylamino) ethyloxy-N$^2$-(10,12-dimethyl-1-oxotetradecyl)ornithine]-5-(3-hydroxyglutamine)-6-(3-hydroxyproline)echinocandin B in a yield of 60 percent.

$^1$H NMR (400 MHz, CD$_3$OD) δ 1.15 (d, 3, J=6.2 Hz, CH$_3$-threo), 2.48 (dd, 1, J=9.5 and 15.4 Hz, H$_{4a}$-glu), 2.80 (dd, 1, J=3.6 and 15.4 Hz, H$_{4b}$-glu), 3.49–3.64 (m, 2, OCH$_2$CH$_2$NHZ), 3.78 (m, OCH$_2$CH$_2$NHZ), 4.08 (m, 1, H$_4$-orn), 4.44 (dd, 1, J=6.7 and 10.7 Hz, H$_2$-orn), 4.98 (d, 1, J=3.6 Hz, H$_2$-threo), 5.06 (s, 2, CH$_2$C$_6$H$_5$), 5.08 (d, 1, J=4.0 Hz, H$_2$-glu), 5.16 (d, 2, J=1.8 Hz, H$_5$-orn), 6.74 (d, 2, J=8.6 Hz, H$_3$ and H$_5$-ArH), 7.13 (d, 2, J=8.6 Hz, H$_2$ and H$_6$-ArH), 7.33 (m, 5, CH$_2$C$_6$H$_5$).

Part B

In a manner similar to Example 2, a solution of the ether above prepared is hydrogenated to obtain 1-[4-hydroxy-5-amino-ethyloxy-N$^2$-(10,11-dimethyl-1-oxotetradecyl) ornithine]-5-(3-hydroxyglutamine-6-(3-hydroxyproline) echinocandin B trifluoroacetate in 90 percent yield.

$^1$H MR (400 MHz, CD$_3$OD) δ 1.16 (d, 3, J=6.2 Hz, CH$_3$-threo), 3.12 (m, 2, OCH$_2$CH$_2$NH$_2$.CF$_3$COOH), 3.72 (m, OCH$_2$CH$_2$NH$_2$.CF$_3$COOH), 4.10 (m, 1, H$_4$-orn), 5.24 (d, 1, J=2.3 Hz, H$_5$-orn); Mass Spectrum: FAB 1108 (MH)$^+$; Anal. Calcd for C$_{52}$H$_{86}$ClN$_9$O$_{17}$: C, 54.56; H, 7.57; N, 11.01; Cl, 3.10. Found: C, 54.28; H, 7.60; N, 10.88; Cl, 3.02.

In operations carried out in a manner similar to Example 1 the following compounds were prepared from pneumocandin B$_0$ and the appropriate R$_1$OH:

EXAMPLE 5
SEQ ID NO 1
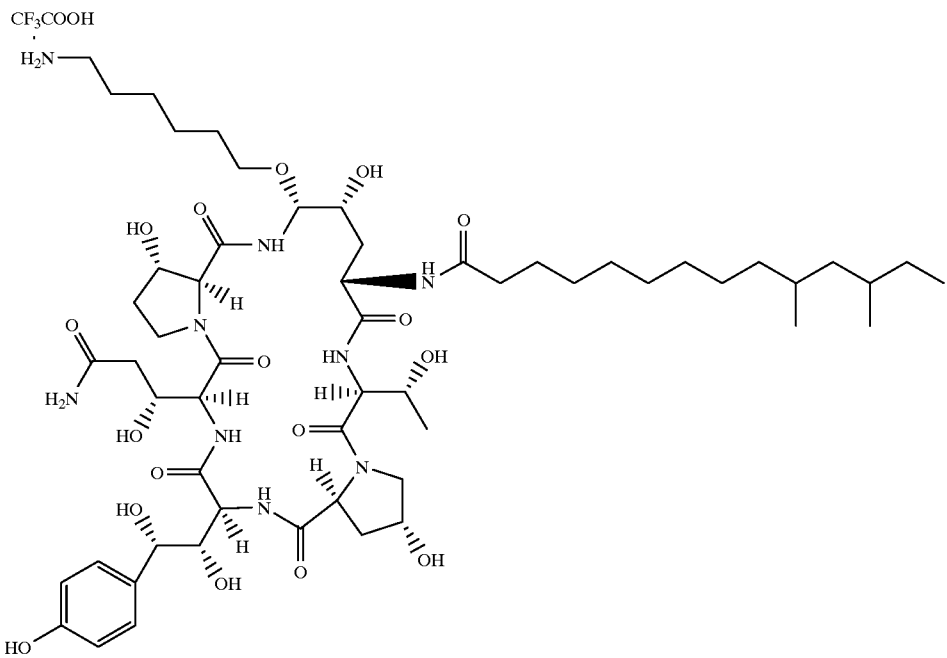
Yield=15%; ¹H NMR (400 MHz, CD$_3$OD) δ 5.10 (m, H$_2$-glu , H$_5$-orn), 2.92 (t, CH$_2$NH$_2$.CF$_3$COOH), 1.59 and 1.41 (m's, OCH$_2$CH$_2$CH$_2$CH$_2$CH$_2$CH$_2$NH$_2$.CF$_3$COOH); FAB-MS (Li) m/z 1170.2 (MLi)$^+$
CHNH$_2$.CF$_3$COOH), 3.47 (m, OCH$_2$), 1.26 (d, CH$_3$CHNH$_2$.CF$_3$COOH); FAB-MS (Li) m/z 1129.0 (MH+ Li)$^+$
EXAMPLE 6
SEQ ID NO 1
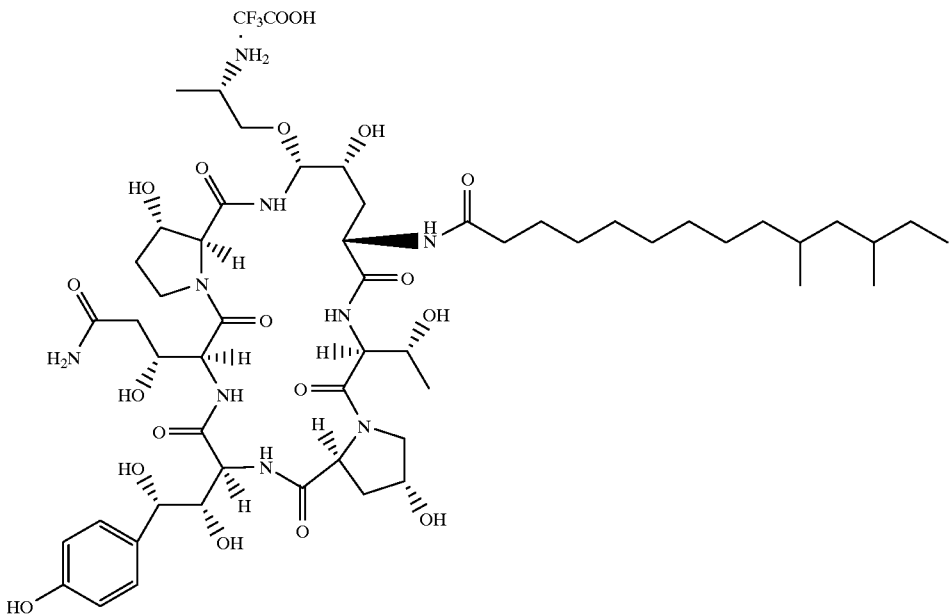
Yield=11%; ¹H NMR (400 MHz, CD$_3$OD) δ 5.26 (d, H$_5$-orn), 5.08 (dd, H$_2$-glu), 4.99 (dd, H$_2$-threo), 3.66 (m,

EXAMPLE 7
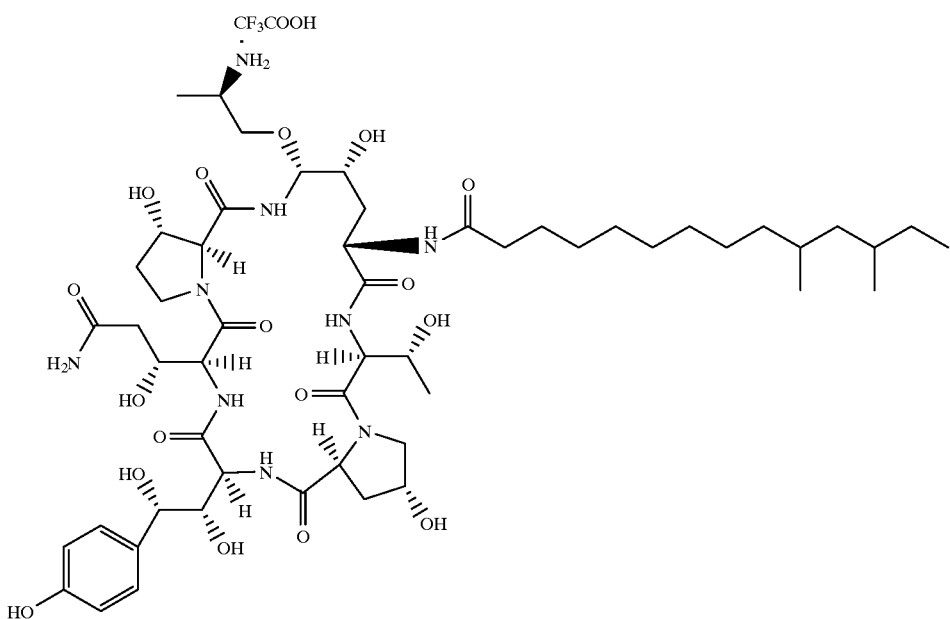
SEQ ID NO 1
Yield=18%; $^1$H NMR (400 MHz, CD$_3$OD) δ 5.25 (dd, H$_5$-orn), 5.08 (dd, H$_2$-glu), 4.99 (dd, H$_2$-threo), 3.73 (m, CHNH$_2$.CF$_3$COOH), 3.48 (m, OCH$_2$), 1.28 (d, CH$_3$ CHNH$_2$ .CF$_3$COOH); FAB-MS (Li) m/z 1129.5 (MH+Li)$^+$ quartet, OCH$_2$), 1.26 (s, (CH$_3$)$_2$CNH$_2$.CH$_3$COOH); FAB-MS (Li) m/z 1142.9 (MLi)$^+$
EXAMPLE 8
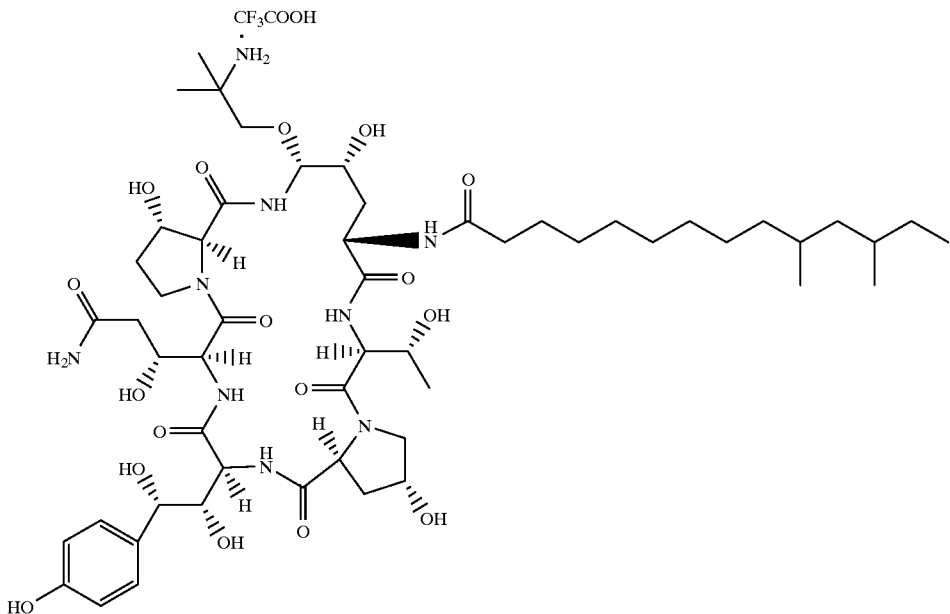
SEQ ID NO 1
Yield=23%; $^1$H NMR (400 MHz, CD3OD) δ 5.22 (d, H5-orn), 5.09 (d, H2-glu), 4.98 (d, H2-threo), 3.45 (AB

EXAMPLE 9
SEQ ID NO 1
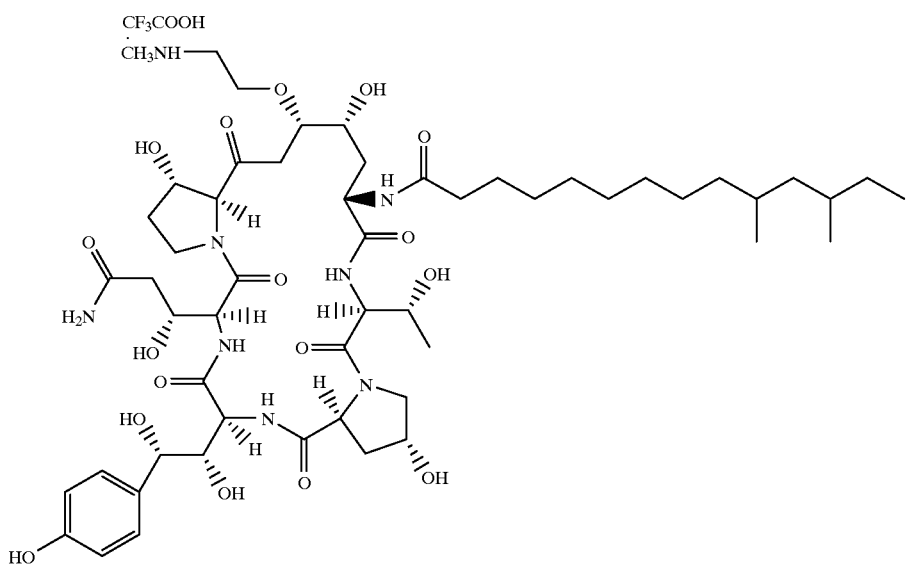
Yield=24%; $^1$H NMR (400 MHz, CD$_3$OD) δ 5.28 (d, H5-orn), 5.08 (d, H2-glu), 4.99 (d, H2-threo), 3.72 (m, OCH2), 3.19 (m, CH$_2$NHCH$_3$.HCl), 2.72 (s, CH$_3$NH.HCl); FAB-MS (Li) m/z 1128.9 (MLi)$^+$
CH$_3$CH$_2$NH.CF$_3$COOH), 1.29 (t, CH$_3$CH$_2$NH.CF$_3$COOH); FAB-MS (Li) m/z 1143.2 (MLi)$^+$
EXAMPLE 10
SEQ ID NO 1
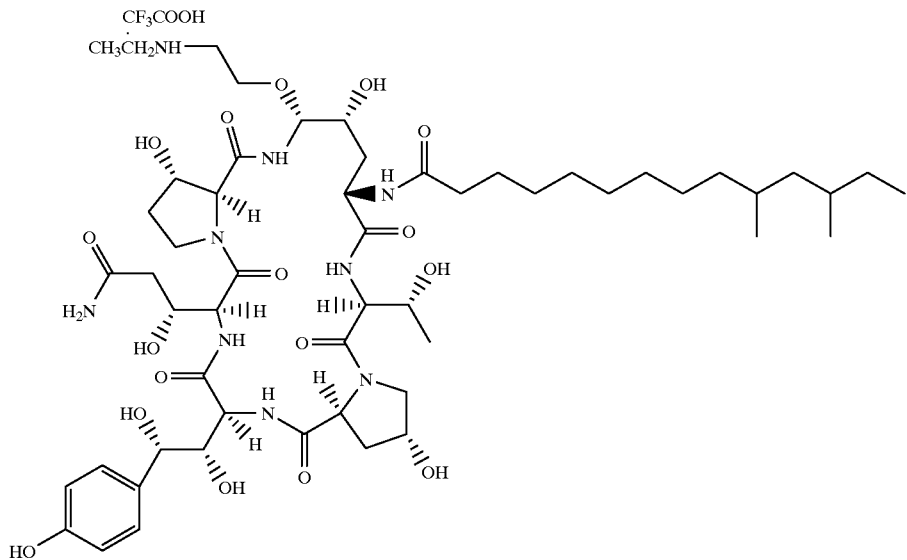
Yield=28%; $^1$H NMR (400 MHz, CD$_3$OD) δ 5.28 (d, H5-orn), 5.08 (dd, H2-glu), 5.00 (dd, H2-threo), 3.73 (m, OCH$_2$), 3.21 (m, CH$_2$NHCH$_2$CH$_3$.CF$_3$COOH), 3.09 (m,

EXAMPLE 11
SEQ ID NO 1
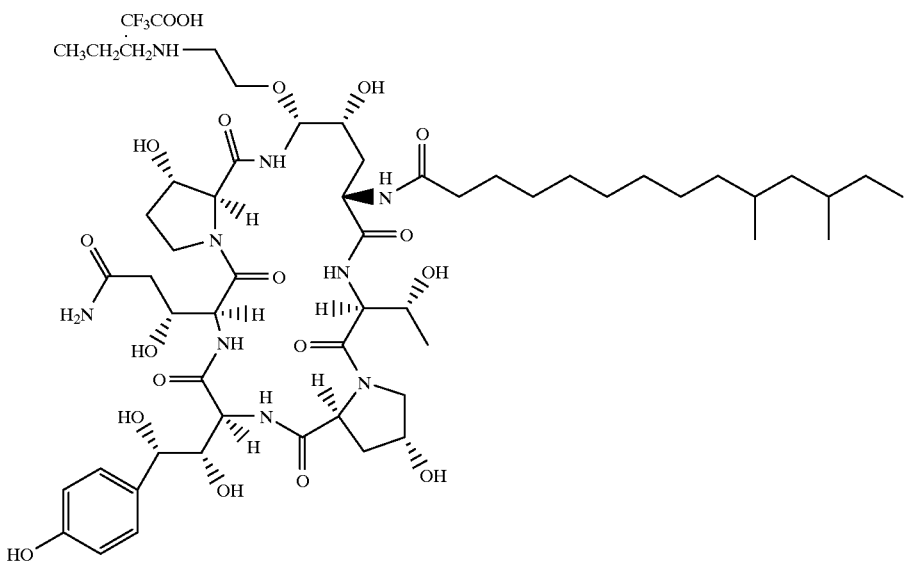
Yield=50%; ¹NMR (400 MHz, CD₃OD) δ 5.28 (d, H5-orn), 5.09 (dd, H2-glu), 5.01 (dd, H2-threo), 3.73 (m, OCH₂), 3.22 (m, CH₂NHCH₂CH₂CH₃.CF₃COOH), 2.98 (m, CH₃CH₂CH₂NH.CF₃COOH), 1.72 (m, CH₃CH₂CH₂NH.CF₃COOH), 1.03 (t, CH₃CH₂CH₂NH.CF₃COOH); FAB-MS (Li) m/z 1156.6 (MLi)⁺
Yield=24%; ¹H NMR (400 MHz, CD₃OD) δ 5.27 (d, H5-orn), 5.11 (dd, H2-glu), 5.01 (m, H2-threo), 3.80 (m, OCH₂ and HOCH₂), 3.24 (m, CH₂NHCH₂CH₂OH.HCl), 3.15 (m, HOCH₂CH₂NH.HCl); FAB-MS (Li) m/z 1158.1 (MLi)⁺
EXAMPLE 12
SEQ ID NO 1
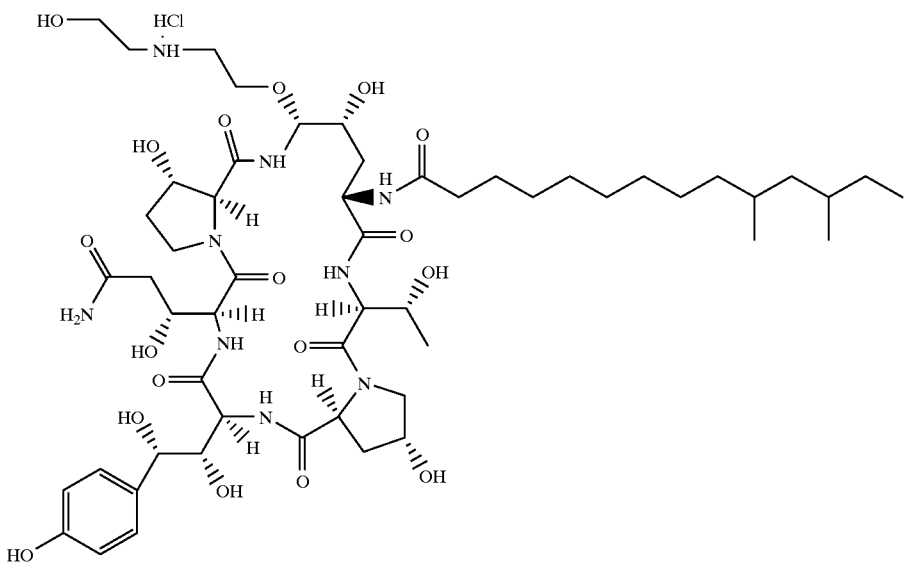

EXAMPLE 13
SEQ ID NO 1
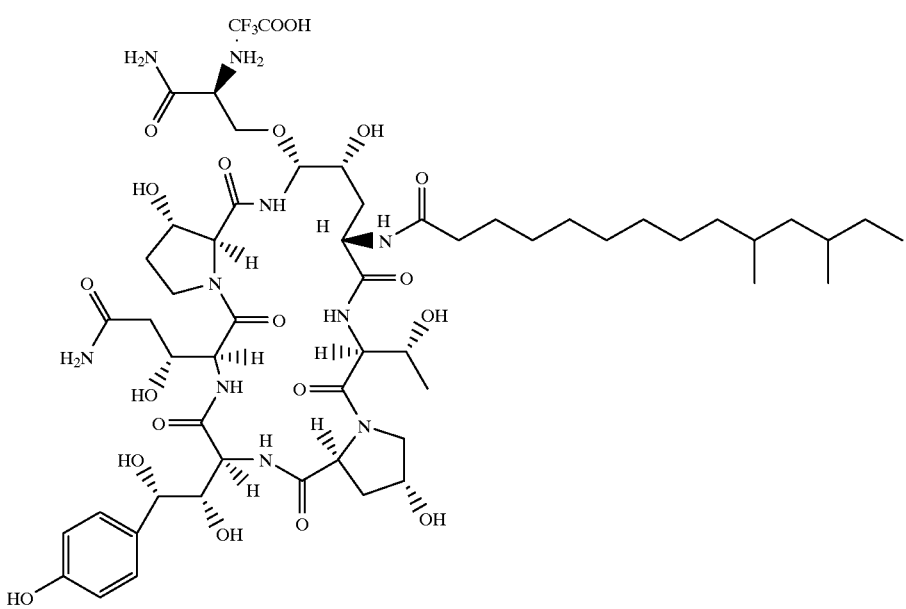
Yield=17%; $^1$H NMR (400 MHz, CD30D) δ 5.25(d, H5-orn), 5.09 (dd, H2-glu), 4.99 (m, H2-threo), 4.29 (m, CHCONH$_2$) 3.88 (m, OCH$_2$); FAB-MS (Li) m/z 1157.6 (MLi)[<s]up+ (MLi)$^+$
EXAMPLE 14
SEQ ID NO 1
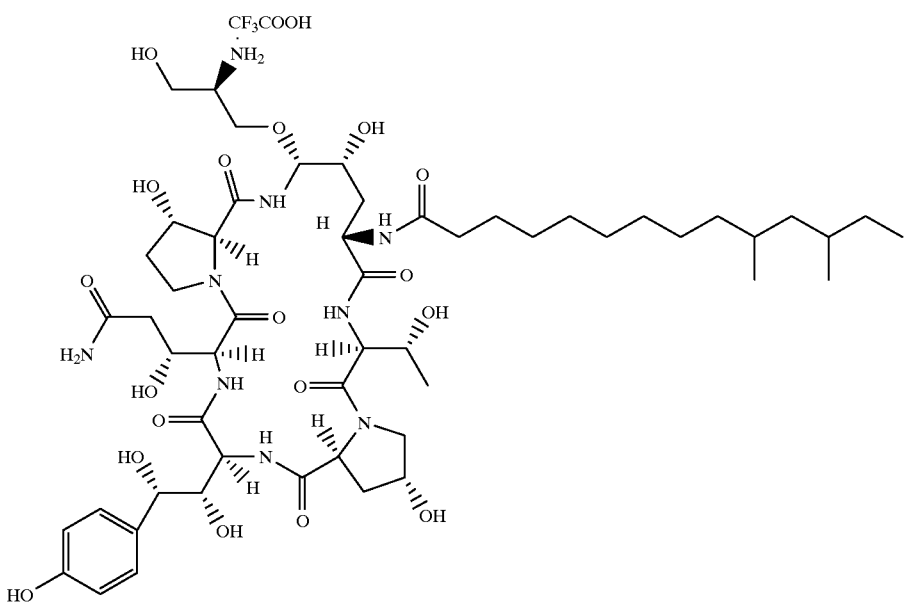
Part A
(R)-2-methoxycarbonyl-2-aminoethyl Ether Trifluoroacetate
Yield=4% $^1$H NMR (400 MHz, CD$_3$OD) δ 5.28 (br s, H5-orn), 5.08 (dd, H2-glu), 4.99 (dd, H2-threo), 3.86 (s, COOCH$_3$), 3.80 (m, OCH$_2$); FAB-MS (Li) mlz 1171.9

Part B (R)-3-hydroxy-2-aminopropyl Ether trifluoroacetate
of above formula

The protected ether prepared in Part A (100 mg, 0.0858 mmol) was suspended in a 1:1 mixture of dioxane/water (15 mL). Sodium borohydride (23 mg, 0.608 mmol) was added and the mixture was stirred at 25° C. for a period of 2 h. The solution was then acidified with 2N HCl and lyophilized. The crude amino alcohol was purified in a manner similar to that described in Example 1 with 35% $CH_3CN/H_2O$ (0.1% $CF_3COOR$) as the mobile phase to give 40 mg of the (R)-serinol ether:

Yield=41%; $^1$H NMR (400 MHz, $CD_3OD$) δ 5.27 (d, H5-orn), 5.08 (dd, H2-glu), 4.99 (m, H2-threo), 3.7 (m, $HOCH_2CH$ $(NH_2.CF_3COOH)CH_2O)$, 3.40 (m, $CHNH_2.CF_3COOH$); FAB-MS (Li) m/z 1145.1$(MLi)^+$

EXAMPLE 15

Part A (s)-2-methoxycarbonyl-2-aminoethyl Ether
Trifluoroacetate

Yield=7%; $^1$H NMR (400 MHz, $CD_3OD$) δ 5.21(br s, H5-orn), 5.09 (dd, H2-glu), 4.98 (dd, H2-threo), 3.85 (s, $COOCH_3$), 3.81 (m, $OCH_2$); FAB-MS (Li) m/z 1172.9(MH+Li)$^+$ Part B (S)-3-hydroxy-2-aminopropyl Ether Trifluoroacetate
of above formula In a manner similar to that described in Example 14, Part B, the (S)-serinol ether is prepared:

$^1$H NMR (400 MHz, $CD_3OD$) δ 5.23 (d, H5-orn), 5.09 (dd, H2-glu), 4.99 (m, H2-threo), 3.7 (m, $HOCH_2CH$ $(NH_2.CF_3COOH)CH_2O)$, 3.39 (m, $CHNH_2.CF_3COOH$); FAB-MS (Li) m/z 1172.9(MH+Li)$^+$

SEQ ID NO 1

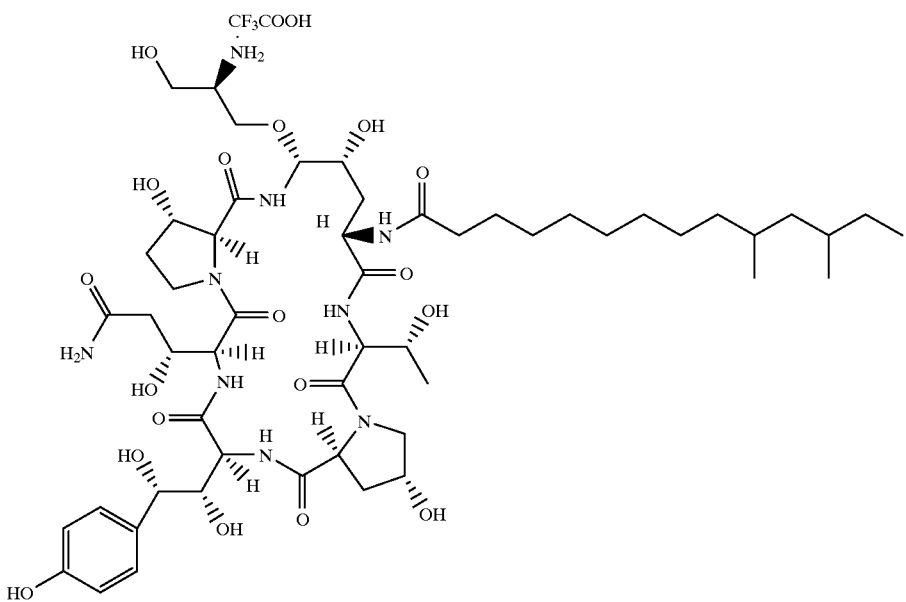

EXAMPLE 16

SEQ ID NO 1

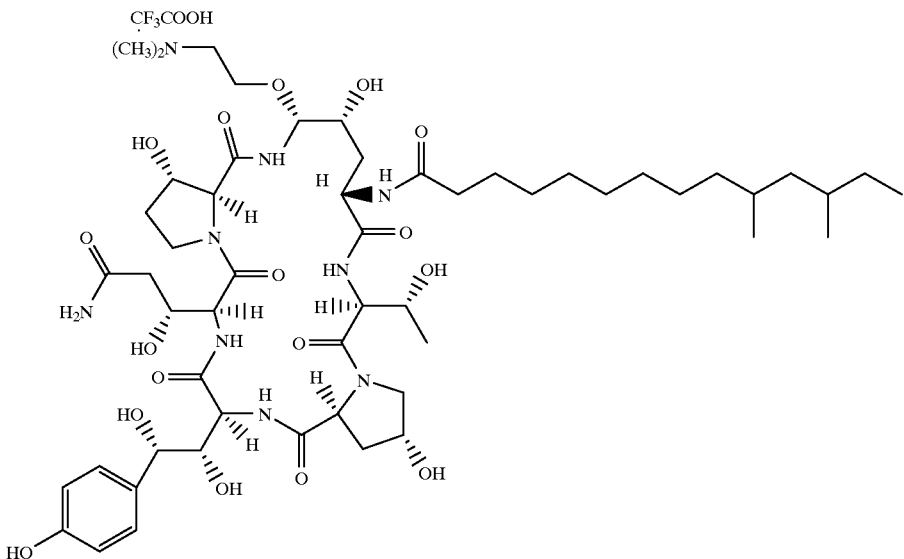

To a stirred solution of the aminoethyl ether of Example 1 as the trifluoroacetate (400 mg, 0.327 mmol) and 530 μL (6.54 mmol) of 37% aqueous formaldehyde in 20 mL of acetonitrile and 10 mL of water was added 62 mg (0.987 mmol) of sodium cyanoborohydride. The reaction mixture was stirred for 15 min and then glacial acetic acid was added to pH 7. The solution was diluted with water (2x) and chromatographed. Reverse-phase (C18) flash column chromatography eluting with 30–50% acetonitrile/water (1% acetic acid) was followed by lyophilization of the product-containing fractions to provide 355 mg of impure compound of the above formula as the acetate. Preparative reverse-phase HPLC (C18) of this material eluting with 40% acetonitrile/water (0.1% trifluoroacetic acid) provided clean dimethylaminoethyl ether as the trifluoroacetate salt:

[1] H NMR (400 MHz, $CD_3OD$) δ 5.31(d, H5-orn), 5.09 (dd, H2-glu), 4.99(dd, H2-threo), 3.78 (m, $OCH_2$), 3.38 (m, $CH_2N(CH_3)_2 \cdot CF_3COOH$), 2.92 and 2.89 (s, s, $(CH_3)_2 N \cdot CF_3COOH$); FAB-MS (Li), m/z 1143.1 $(MLi)^+$, 1053.9

EXAMPLE 17

SEQ ID NO 1

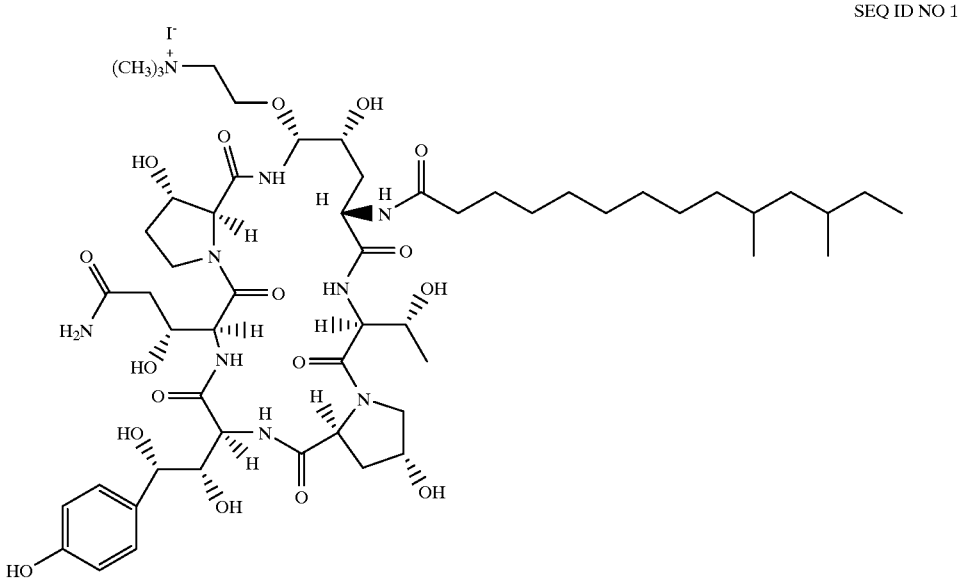

To a stirred solution of the compound of Example 16 (150 mg, 0.125 mmol) in N,N-dimethylformamide (10 mL) and 1M sodium bicarbonate (2 mL, 2 mmol) was added iodomethane (2 mL, 32.1 mmol). The reaction mixture was stirred for a period of 18 h. The mixture was diluted with water (2x) and chromatographed. Reverse-phase (C18) flash column chromatography elating with 30–50% acetonitrile/ water was followed by lyophilization of the product-containing fractions to provide 83 mg of the quaternary salt having the above formula.

Yield=52%; $^1$H NMR (400 MHz, CD$_3$OD) δ 1.18 (d, 3, CH$_3$-threo), 3.19 (m, 11, OCH$_2$CH$_2$N$^+$(CH$_3$)$_3$), 3.58 (m, 2, OCH$_2$), 4.98 (d, 1, H$_2$-threo), 5.08 (d, 1, H$_2$-glu), 5.29 (d, 1, H$_5$-orn, 6.75 (d, 2, H$_3$ and H$_5$-ArH), 7.13 (d, 2, H$_2$ and H$_6$-ArH); FAB-MS (Li) m/z 1150.8 (M$^{+)}$

EXAMPLE 18

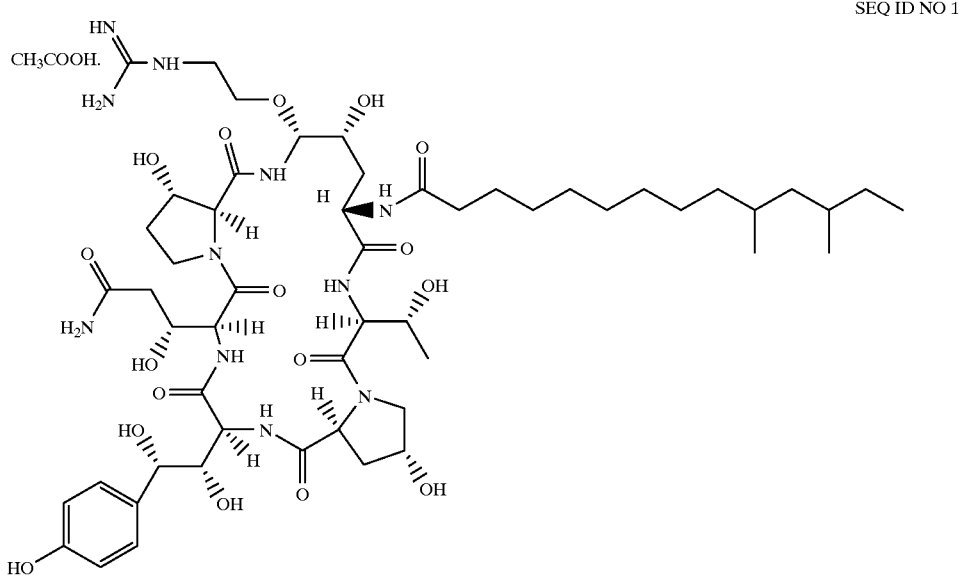

To a stirred solution of the aminoethyl ether of Example 1 as the acetate (160 mg, 0.137 mmol) and 1M sodium bicarbonate (150 μL, 0.150 mmol) in absolute methanol (5 mL) was added aminoiminomethanesulfonic acid (30 mg, 0.242 mmol). After a period of 1.5 h, the solvent was removed in vacuo. Preparative reverse-phase HPLC (C18) of the residue, eluting with 45% acetonitrile/water (0.1% acetic acid), was followed by lyophilization of the product-containing fractions to produce the 5-guanidinoethyl ether as the acetate (100 mg):

Yield=60%; $^1$H NMR (400 MHz, CD$_3$OD) δ 3.32 (m, OCH$_2$CH$_2$NHC(=NH)NH$_2$, 3.62 (m, OCH$_2$), 5.01 (d, H$_2$-threo), 5.09 (d, H$_2$-glu), 5.18(d, H$_5$-orn); FAB MS(Li) m/z 1053.9

SEQ ID NO 1

EXAMPLE 19

SEQ ID NO 1

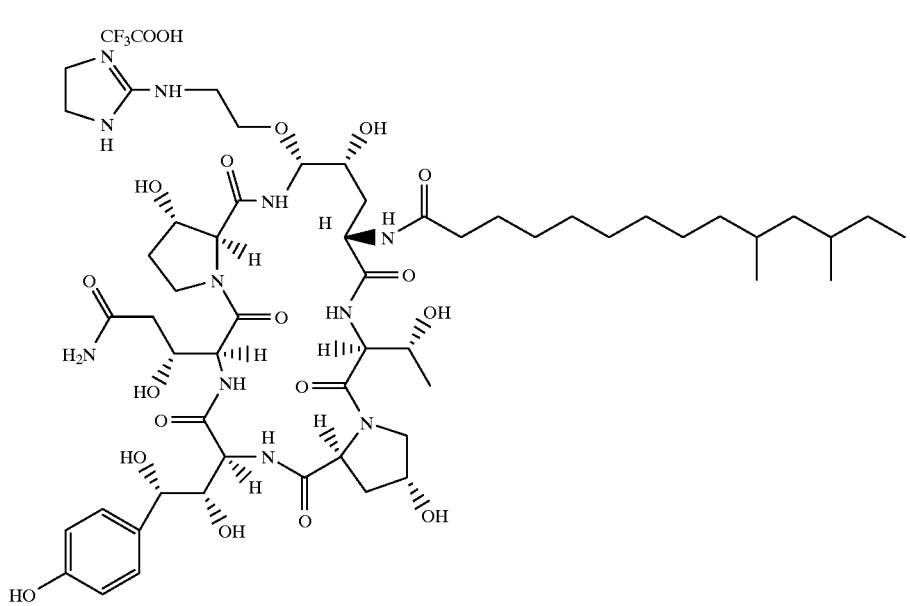

A solution of the aminoethyl ether of Example 1 as the acetate (724 mg, 0.680 mmol), 2-methylthio-2-imidazoline hydroiodide (167 mg, 0.682 mmol) and 1M aqueous NaHCO$_3$ (1.4 mL) in methanol (5 mL) was heated under reflux for 4.5 h and then concentrated to dryness. Preparative reverse-phase HPLC (C18) of the residue eluting with 35–40% acetonitrile/water (0.1% trifluoroacetic acid) was followed by lyophilization of the product-containing fractions to give the cyclic guanidine (100 mg) substituted aminoethyl ether of above formula:

Yield=25% $^1$H NMR (400 MHz, CD$_3$OD) δ 3.36 (t, OCH$_2$CH$_2$), 3.64 (m, OCH$_2$), 3.69 (s, NCH$_2$CH$_2$N), 4.98 (dd, H$_2$-threo), 5.09 (dd, H$_2$-glu), 5.18 (dd, H$_5$-orn); FAB MS(Li) m/z 1054.4

EXAMPLE 20

To a stirred solution of the aminoethyl ether of Example 1 as the acetate (150 mg, 0.128 mmol) and 1N sodium hydroxide (130 μL, 0.130 mmol) in water (5 mL) and N,N-dimethylformamide (5 mL) was added ethylacetimidate hydrochloride (160 mg, 1.29 mmol). After a period of 18 h at pH 8.5, glacial acetic acid was added to pH 7. Reverse-phase (C18) flash column chromatography of the neutralized reaction mixture, eluting with acetonitrile/water, was followed by lyophilization of the product-containing fractions. Preparative reverse-phase (C18) HPLC of this material, eluting with acetonitrile/water (0.1% acetic acid), was followed by lyophilization of the product-containing fractions to give the acetamidine (26 mg) having the above formula:

Yield=17%; $^1$H NMR (400 MHz, CD$_3$OD) δ 1.17 (d, 3), 2.23 (s, 3), 3.42 (m, 2), 3.69 (m, 2), 4.06 (m, 1), 4.98 (dd, 1), 5.08 (dd, 1), 5.22 (d, 1); FAB MS(Li), m/z 1053.6

SEQ ID NO 1

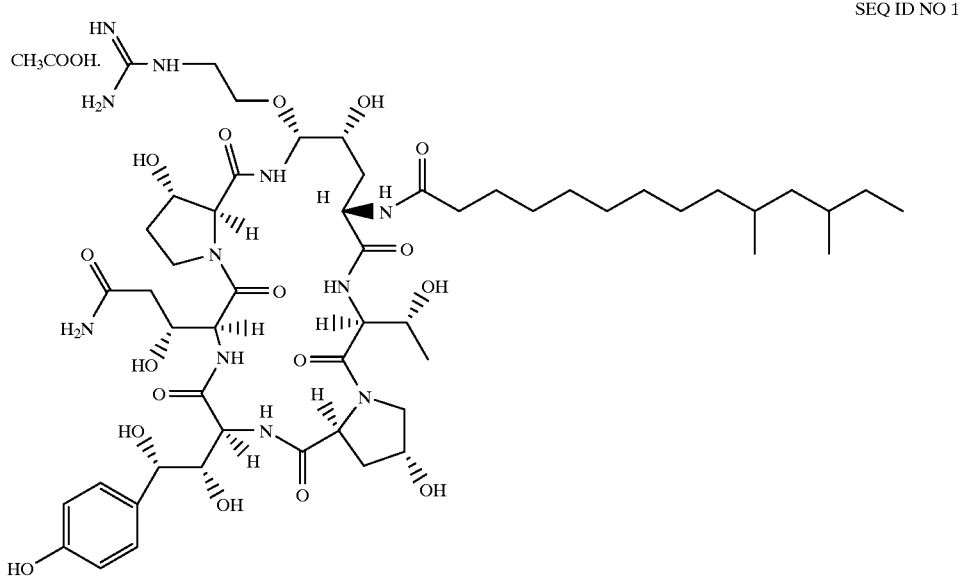

EXAMPLE 21

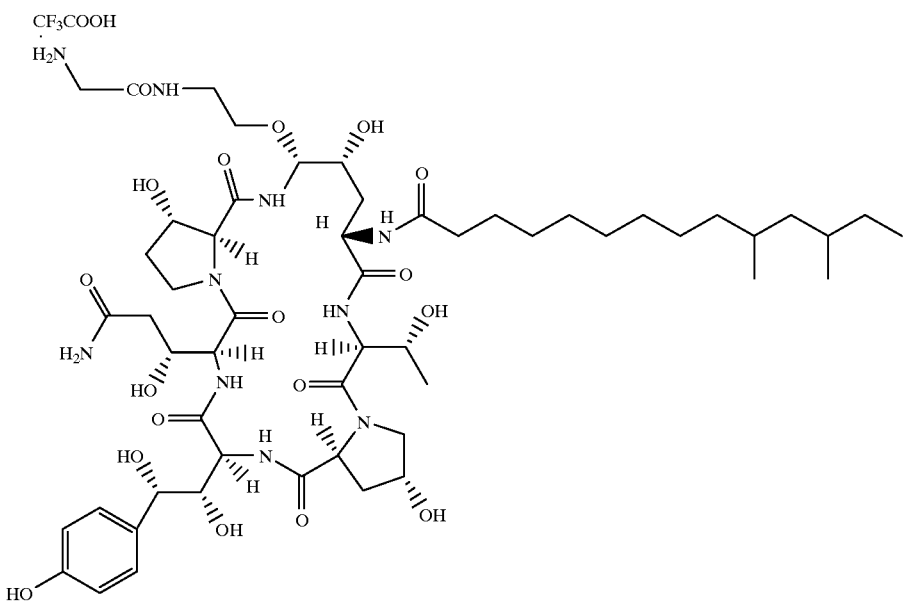

SEQ ID NO 1

Part A

(N-benzyloxycarbonylglycyl)aminoethyl Ether

The aminoethyl ether of Example 1 as the acetate (210 mg, 0.180 mmol) was dissolved in N,N-dimethylformamide (2 mL). To this solution 1M sodium bicarbonate (200 μL, 0.200 mmol) and pentafluorophenyl N-benzyloxycarbonylglycinate (106 mg, 0.270 mmol) were added. After 1 h, the reaction mixture was diluted with water (2×). Isolation by reverse-phase (C18) flash column chromatography eluting with 50–80% acetonitrile/water gave, after lyophilization of the product-containing fractions, the N-CBZ glycine conjugate of the above formula was obtained (130 mg):

Yield=56%; FAB-MS (Li), m/z 1306.4 (MLi)$^+$

Part B

Glycylaminoethyloxy Ether as the Trifluoroacetate

The above ether was obtained from the N-benzyloxycarbonylglycyl)aminoethyl ether (Part A) in a manner similar to that described above (Example 4, Part B):

Yield=49%; FAB-MS (Li), m/z 1171.7 (MLi)$^+$

EXAMPLE 22

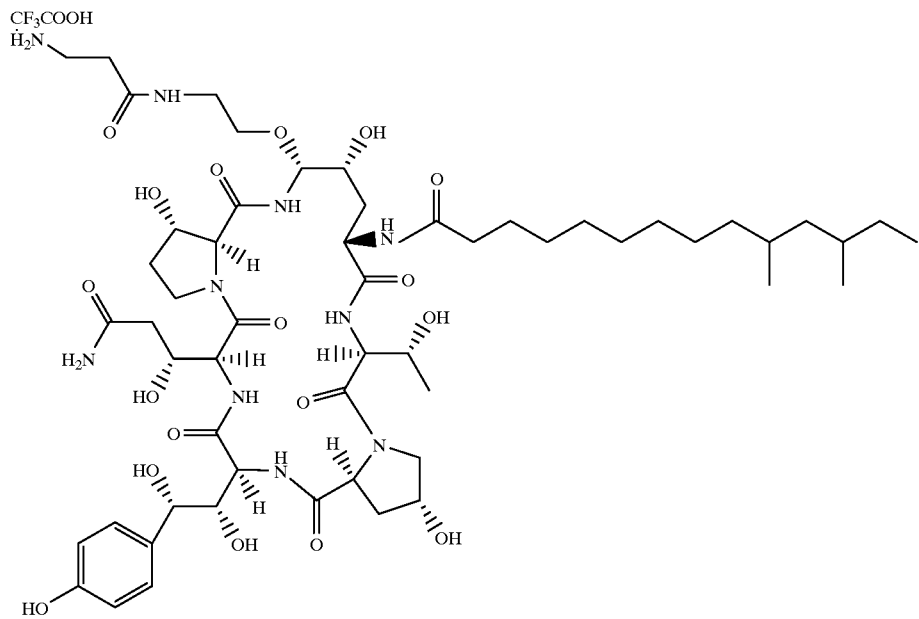

SEQ ID NO 1

In operations carried out in a manner similar to that described in Example 21, (β-alanyl)-aminoethyloxy trifluoroacetate was prepared:

$^{1}$H NMR (400 MHz, CD$_3$OD) δ 5.13 (d, H5-orn), 5.08 (dd, H2-glu), 4.98 (dd, H2-threo), 3.58 (m, OCH$_2$), 3.41 and 3.32 (m, m, CH$_2$NHCO), 261 (t, NHCOCH$_2$). FAB-MS (L), m/z 1185.5 (MLi)$^{+}$.

In operations carried out in a manner similar to Example 4 (Parts A and B), the following compounds were prepared:

EXAMPLE 23

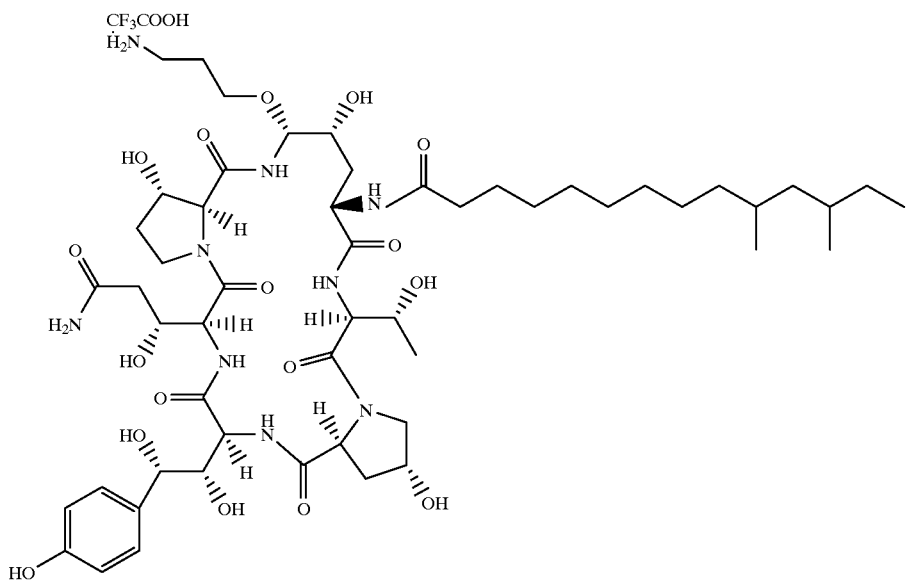

SEQ ID NO 1

FAB-MS (Li) m/z 1128.7 (MLi)$^{+}$

EXAMPLE 24
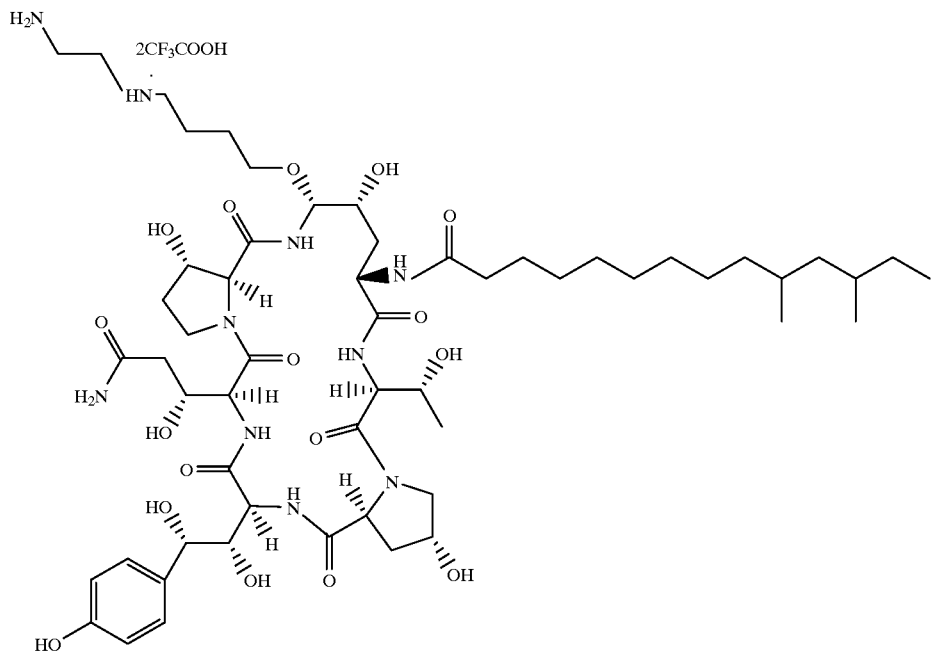
FAB-MS (Li) m/z 1157.7 (MLi)+
SEQ ID NO 1
EXAMPLE 25
SEQ ID NO 1
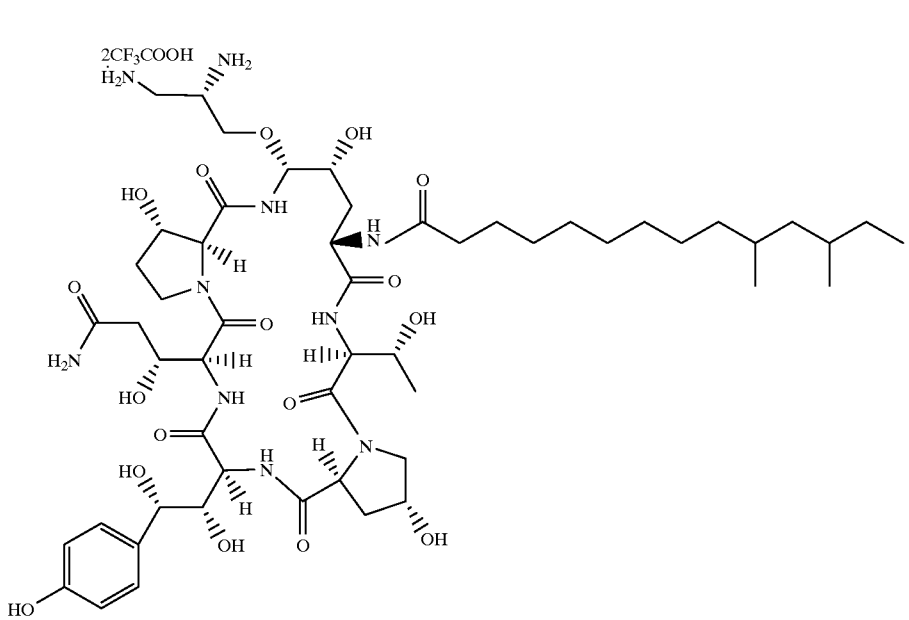
FAB MS (Li) m/z 1143.7 (MLi)+

EXAMPLE 26

SEQ ID NO 1

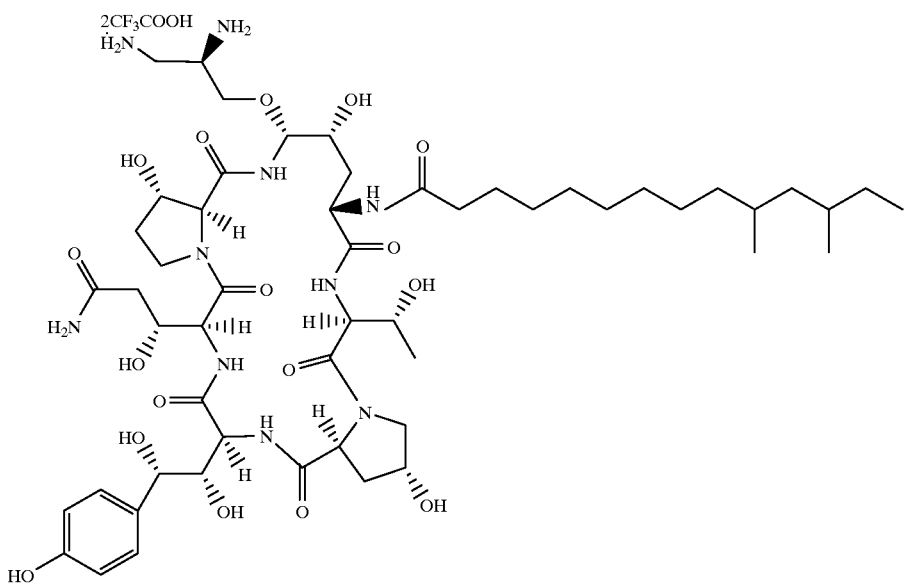

FAB MS (Li) m/z 1143.8 (MLi)$^+$

The foregoing examples are illustrated in the preferred stereoisomeric form.

EXAMPLE 27

1000 hard gelatin capsules, each containing 500 mg of compound of Example 1 are prepared from the following formulation:

| Compound | Grams |
| --- | --- |
| Compound of Example 1 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 28

An aerosol composition may be prepared having the following formulation:

| | Per Canister |
| --- | --- |
| Compound of Example 1 | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE 29

1000 compressed tablets each containing 500 mg of compound of Example 2 are prepared from the following formulation:

| Compound | Grams |
| --- | --- |
| Compound of Example 2 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

PREPARATION OF STARTING MATERIAL

The starting material 1-[4,5-dihydroxy-N$^2$-(10,12-dimethyl-1-ozotetradecyl)ornithine]-5-(3-hydroxyglutamine)-6-(3-hydroxyproline)echinocandin B may be obtained by cultivating Z. arboricola ATCC 20868 in a nutrient medium enriched in mannitol as the primary source of carbon as described in U.S. Pat. No. 5,021,341, Jun. 4, 1991.

The starting material of Example 2, 1-[4,5-dihydroxy-N$^2$-(4-octyloxybenzoyl)ornithine]-5-(3 hydroxyglutamine)-6-(3-hydroxyproline)echinocandin B may be prepared as described in EPA 447 186 A1, published Sep. 18, 1991.

The starting material in Example 3 , 1-(4,5-dihydroxyornithine)-5-(3-hydroxyglutamine)-6-(3-hydroxyproline)echinocandin B may be prepared as described in EPA 451 957 A2, published Oct. 16, 1991.

What is claimed is:

1. A compound having the formula (SEQ ID NO 1)

wherein:

$R_1$ is —$CH_2CH(NH_2)CH_2R^I$

—$C_nH_{2n}NR^{II}R^{III}$

—$(CH_2)_{1-3}CH(NH_2)R^{IV}$ or

—$C_nH_{2n}NHR^V$ wherein n is 2 to 6;

$R_2$ is
- $C_9$–$C_{21}$ alkyl,
- $C_9$–$C_{21}$ alkenyl,
- $C_1$–$C_{10}$ alkoxyphenyl, or
- $C_1$–$C_{21}$ alkoxynaphthyl;

$R^I$ is
— OH
— $NH_2$
— $NHC(=NH)NH_2$
— $NHC(=NH)(CH_2)_{0-3}H$ $R^{II}$ is
— H
- $C_1$–$C_4$ alkyl or
- benzyl $R^{III}$ is
— H
- $C_1$–$C_4$ alkyl
- benzyl or
$R^{II}$ and $R^{III}$ together are —$(CH_2)_4$— or
—$(CH_2)_5$—

$R^{IV}$ is
- $C_1$–$C_4$ alkyl
—$CONH_2$ $R^V$ is
—$C(=NH)NH_2$
—$C(=NH)(CH_2)_{0-3}H$
—$(CH_2)_{2-4}NH_2$
—$(CH_2)_{2-4}OH$
—$CO(CH_2)_{1-3}NH_2$
—$(CH_2)_{2-4}NH(C=NH)NH_2$
—$(CH_2)_{2-4}NH(C=NH)(CH_2)_{0-3}H$ or and pharmaceutically acceptable salts thereof.

2. A compound in accordance with claim 1 wherein $R_2$ represents —$C_{9-21}$ alkyl.

3. A compound in accordance with claim 2 wherein $R_2$ represents 9,11-dimethyldecyl.

4. A compound according to claim 3 wherein $R_1$ is $C_nH_{2n}NR^{II}R^{III}$, with n equal to 2 and $R^{II}$ and $R^{III}$ equal to H, and $R_2$ is 9,11-dimethyltridecyl.

5. A compound according to claim 3 wherein $R_1$ is $C_nH_{2n}NR^{II}R^{III}$, with n equal to 2 and $R^{II}$ and $R^{III}$ equal to H, and $R_2$ is —$C_6H_4OC_8H_{17}$.

6. A compound according to claim 3 wherein $R_1$ is $C_nH_{2n}NR^{II}R^{III}$, with n equal to 2 and $R^{II}$ and $R^{III}$ equal to H, and $R_2$ is —$C_{10}H_6OC_8H_{17}$.

7. A compound according to claim 3 wherein $R_1$ is $C_nH_{2n}NR^{II}R^{III}$, with n equal to 3 and $R^{II}$ and $R^{III}$ equal to H, and $R_2$ is 9,11-dimethyltridecyl.

8. A compound according to claim 3 wherein $R_1$ is $CH_2CH(NH_2)CH_2R^I$ and $R^I$ is $NH_2$, and $R_2$ is 9,11-dimethyltridecyl.

9. A compound according to claim 3 wherein $R_1$ is $C_nH_{2n}NHR^V$, with n equal to 2, and $R^V$ equal to —$(CH_2)_{2-4}NH_2$, and $R_2$ is 9,11-dimethyltridecyl.

10. A compound according to claim 1 wherein $R_1$ is —$CH_2CH(NH_2)CONH_2$.

11. A compound according to claim 4 which is of the following stereochemical configuration (SEQ ID NO 1)

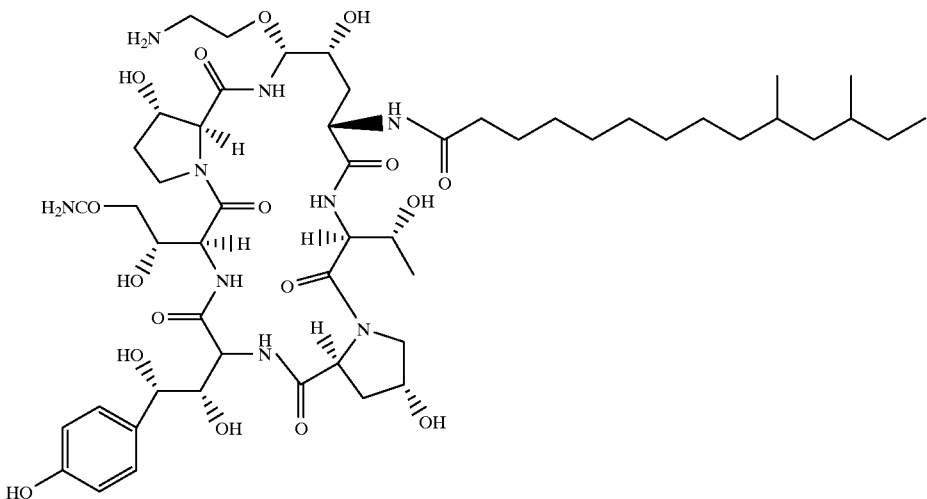

12. An antibiotic composition comprising a therapeutic amount of a compound of claim 1 in a pharmaceutically acceptable carrier.

13. A composition according to claim 12 in unit dosage form wherein the compound is present in an amount of 10 milligrams to 200 milligrams.

14. A method for controlling microbial infections in a mammal in need of such treatment comprising administering to said mammal a therapeutic amount of the compound of claim 1.

15. A compound having the formula

SEQ ID NO 1

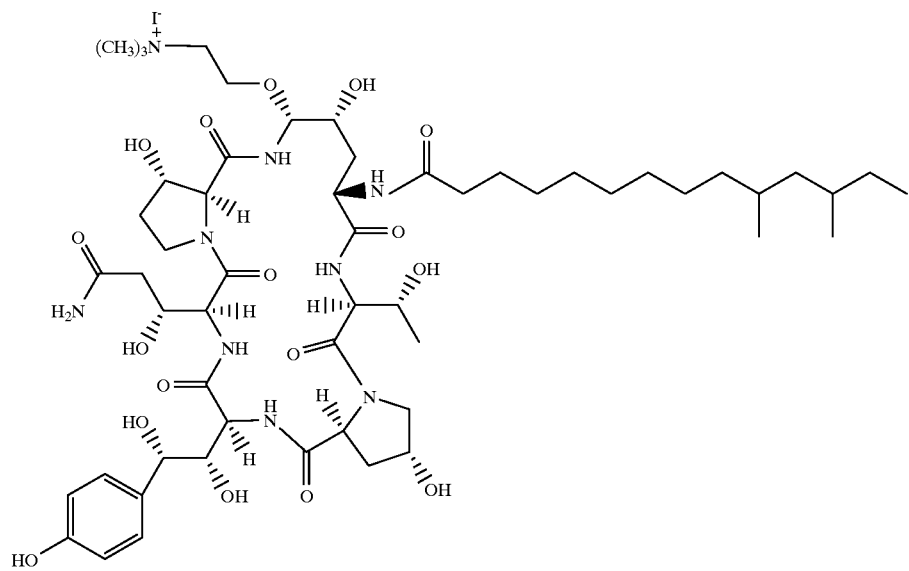

* * * * *

UNITED STATES PATENT AND TRADEMARK OFFICE
CERTIFICATE OF CORRECTION

PATENT NO. : 5,914,313
DATED : June 22, 1999
INVENTOR(S) : Frances Aileen Bouffard and James F. Dropinski It is certified that error appears in the above-identified patent and that said Letters Patent is hereby corrected as shown below:

In claim 1, column 41, delete line 62, and replace it with the following:

-- $-C_1-C_{10}$ alkoxynaphthyl; --

Signed and Sealed this

Eighteenth Day of January, 2000

Attest:

Q. TODD DICKINSON

*Attesting Officer*          *Commissioner of Patents and Trademarks*

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 1:

```
Xaa Thr Xaa Xaa Xaa Xaa
 1               5
```